(12) United States Patent
Azam et al.

(10) Patent No.: US 11,771,494 B2
(45) Date of Patent: Oct. 3, 2023

(54) ELECTROSURGICAL APPARATUS

(71) Applicant: Medtronic, Inc., Minneapolis, MN (US)

(72) Inventors: Suleman Azam, Waterloo (CA); Ryan Vadori, Guelph (CA); Carolyn Holladay, York (CA); Robert Harrison, Milton (CA)

(73) Assignee: Medtronic, Inc., Minneapolis, MN (US)

( * ) Notice: Subject to any disclaimer, the term of this patent is extended or adjusted under 35 U.S.C. 154(b) by 548 days.

(21) Appl. No.: 16/723,310

(22) Filed: Dec. 20, 2019

(65) Prior Publication Data

US 2020/0197087 A1    Jun. 25, 2020

Related U.S. Application Data

(60) Provisional application No. 62/782,723, filed on Dec. 20, 2018.

(51) Int. Cl.
*A61B 18/14* (2006.01)
*A61B 17/34* (2006.01)
(Continued)

(52) U.S. Cl.
CPC ...... *A61B 18/1492* (2013.01); *A61B 17/3423* (2013.01); *A61B 2017/00867* (2013.01);
(Continued)

(58) Field of Classification Search
CPC ............ A61B 18/1402; A61B 18/1477; A61B 18/1492; A61B 2018/00077;
(Continued)

(56) References Cited

U.S. PATENT DOCUMENTS 5,433,739 A * 7/1995 Sluijter .............. A61B 18/1482
607/113
6,146,380 A * 11/2000 Racz .................... A61N 1/0551
606/41
(Continued)

FOREIGN PATENT DOCUMENTS

EP    2692306 A1    2/2014

OTHER PUBLICATIONS

International Preliminary Report on Patentability from PCT Application No. PCT/US2019/067963, dated Jul. 1, 2021, 9 pgs.
(Continued)

*Primary Examiner* — Michael F Peffley
(74) *Attorney, Agent, or Firm* — Patterson Thuente IP (57) ABSTRACT

A method and apparatus for creating lesions in a tissue comprising a puncturing member and a probe. The puncturing member comprises a body with a proximal portion comprising a hub, a distal portion comprising a conductive tip, and a lumen extending between the proximal and distal portion. The probe comprises a handle at the proximal end and a probe body, wherein the probe body is dimensioned to extend through the lumen of the puncturing member, and wherein the probe body comprises at least one displacement portion that is biased to contact the inner wall of the puncturing member when the probe is inserted into the
(Continued)

puncturing member, whereby when the probe body contacts the inner wall, energy is delivered from the probe to the conductive tip of the puncturing member.

15 Claims, 8 Drawing Sheets

(51) Int. Cl.
  *A61B 17/00* (2006.01)
  *A61B 18/00* (2006.01)
(52) U.S. Cl.
  CPC ............... *A61B 2018/00077* (2013.01); *A61B 2018/00577* (2013.01); *A61B 2018/00821* (2013.01)
(58) Field of Classification Search
  CPC ........... A61B 2018/00278; A61B 2018/00196; A61B 2018/00577; A61B 2018/00821; A61B 2018/1475
  See application file for complete search history.

(56) References Cited

U.S. PATENT DOCUMENTS

| | | | |
|---|---|---|---|
| 6,726,684 B1* | 4/2004 | Woloszko | A61B 18/148 606/41 |
| 7,976,542 B1* | 7/2011 | Cosman | A61B 18/1477 606/41 |
| 8,939,969 B2 | 1/2015 | Temelli et al. | |
| 9,717,552 B2 | 1/2017 | Cosman et al. | |
| 10,136,942 B1* | 11/2018 | Cosman, Jr. | A61B 18/1477 |
| 11,116,562 B2* | 9/2021 | Wegrzyn, III | A61B 18/1477 |
| 2003/0144656 A1 | 7/2003 | Ocel et al. | |
| 2014/0066917 A1* | 3/2014 | Cosman, Jr. | A61B 18/1477 606/33 |
| 2014/0276789 A1 | 9/2014 | Dandler et al. | |
| 2017/0209207 A1 | 7/2017 | Devries et al. | |
| 2017/0319259 A1 | 11/2017 | Dunning | |

OTHER PUBLICATIONS

International Search Report and Written Opinion for International Application No. PCT/US2019/067963, dated Apr. 20, 2020.

* cited by examiner

ELECTROSURGICAL APPARATUS

CROSS-REFERENCE TO RELATED APPLICATIONS

This application claims the benefit of U.S. Provisional Patent Application No. 62/782,723, filed Dec. 20, 2018, the entire contents of which is hereby incorporated by reference.

FIELD

The present disclosure relates to radiofrequency probe devices, and more particularly to devices for use with cannulas for delivering radiofrequency energy to a target tissue.

BACKGROUND

Chronic pain is commonly defined as pain lasting longer than three months. Chronic pain may result from an illness and be caused by an initial injury. In many cases, there is no clear cause. The quality of a patient's life can be reduced as the levels of pain increase. Additional health problems may arise due to chronic pain such as sleep disturbance, limitation in movement and mobility, strength, stamina, depression, anxiety, and fatigue. When chronic pain is localized, it may be connected to a particular nerve or set of nerves.

Radiofrequency ablation (RFA) has been shown to relieve localized pain in many patients. RFA can also be used to ablate tumors or dysfunctional tissue. An RFA involves puncturing the patient's skin with a cannula, creating a pathway to the target nerve. The distal tip of the cannula is positioned proximate the target nerve. The cannula is made from a conductive material. A radiofrequency probe, also made from a conductive material, is inserted into the cannula. While inserted, the probe makes contact with the inner wall of the cannula, resulting in electrical contact between the probe and cannula. A generator, connected to the probe, creates a radiofrequency signal which is delivered to the target nerve via the probe and cannula. The increase in tissue temperature causes a lesion on the nerve leading to radiofrequency neurotomy (dissection or cutting of the nerve) and blocks the pain signals to the brain.

The probes used in RFA are typically about 28 gauge (approximately 1 Fr). This gauge size results in the probe being flexible and floppy. The size of the cannula being used in the procedure is dependent on the size of the lesion being formed. Typical cannula sizes can range from about 22 gauge to 16 gauge (approximately 2 Fr to 5 Fr). The result is a probe diameter being substantially less than the cannula lumen diameter.

In some instances, the contact between the inner wall of the cannula and probe is unreliable or poor. This is due to the fact that the probe diameter is substantially less than the cannula lumen diameter. Unreliable or poor contact between the probe and inner wall of the cannula is difficult to detect and the result is intermittent or inconsistent delivery of radiofrequency energy. Without consistent and reliable delivery of energy to the active distal tip, it is difficult to determine whether a lesion of appropriate size has been formed. In some cases, the procedure may appear to have been performed successfully, however, the poor contact may result in ineffective treatment (i.e., small lesion formation or no lesion formation).

SUMMARY

The techniques of this disclosure generally relate to radiofrequency probe devices, and more particularly to devices for use with cannulas for delivering radiofrequency energy to a target tissue.

In one aspect, the present disclosure provides an electrosurgical apparatus for creating lesions in a tissue, the apparatus comprising a puncturing member including a body comprising a proximal portion and distal portion, wherein the distal portion comprises a conductive tip, a hub proximal of the body comprising a connecting means, and a lumen defined by the body and the hub, wherein the lumen extends along the length of the puncturing member. The apparatus further includes a probe comprising a probe body, wherein the probe body is dimensioned to extend through the lumen of the puncturing member, and wherein the probe body comprises at least one displacement portion, and a handle at a proximal end of the probe. When the at least one displacement portion of the probe is disposed within the lumen of the puncturing member, the at least one displacement portion of the probe is biased to contact the inner wall of the puncturing member, whereby when the probe body contacts the inner wall, energy is delivered from the probe to the conductive tip of the puncturing member.

In another aspect, the disclosure provides an electrosurgical device insertable into a lumen of a puncturing member wherein the puncturing member comprises a hub and a conductive distal tip with the lumen extending from the hub to the distal tip. The electrosurgical device includes a body comprised of a conductive material, wherein the body comprises at least one displacement portion wherein when the at least one displacement portion of the probe is disposed within the lumen of the puncturing member, the at least one displacement portion of the probe is biased to contact the inner wall of the puncturing member, whereby when the body contacts an inner wall of the puncturing member, energy is delivered from the body to the conductive tip of the puncturing member.

In another aspect, the disclosure provides an electrosurgical apparatus for creating lesions in a tissue, the electrosurgical apparatus including a puncturing member comprising a body comprising a proximal portion and distal portion, wherein the distal portion comprises a conductive tip, a hub proximal of the body, comprising a connecting means, and a lumen defined by the body and the hub, wherein the lumen extends along the length of the puncturing member. The apparatus further includes a biasing member positioned inside the lumen and a probe comprising a probe body comprised of a conductive material, wherein the probe body is dimensioned to extend through the lumen of the puncturing member. The probe body interacts with the biasing member, such that the biasing member biases the probe body to contact an inner wall of the puncturing member, whereby when the probe body contacts the inner wall, energy is delivered from the probe to the conductive tip of the puncturing member, and a handle at a proximal end of the probe.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

In order that the disclosure may be readily understood, embodiments of the disclosure are illustrated by way of examples in the accompanying figures, in which.

DETAILED DESCRIPTION

During radiofrequency ablation (RFA), a cannula with a conductive distal tip is positioned at the target nerve in a patient. A thin, straight, radiofrequency probe comprising an electrode which is connected to a radiofrequency energy generator is inserted into the cannula. While inserted, the probe makes contact with the inner wall of the cannula, resulting in electrical communication between the probe and cannula. The probe delivers radiofrequency energy from the generator to the distal tip of the cannula and into the target nerve. Depending on the size of lesion required, various cannula gauges are used during this procedure. During procedures with larger gauge cannulas, contact between the probe and inner wall of the cannula may be unreliable or poor leading to ineffective or unsuccessful treatment.

In order to achieve continuous and sustained contact between a probe and the inside wall of a cannula, users may bend the probe body prior to insertion. However, this may result in uncertainty as to whether the apparatus is functioning normally because there is no guarantee that manually bending the straight probes result in a good or reliable contact. Additionally, bending the straight probes risks damaging the probe (e.g., damage to internal components or plastic deformation of the probe body) which could result in a malfunction. Accordingly, there is a need for a probe which will ensure contact with the inner cannula wall when inserted in order to ensure contact between the probe and the inside wall of the cannula to ensure the active distal tip of the cannula supplies continuous and sustained radiofrequency energy to a target nerve.

The problem of unreliable or poor contact between the inner wall of the cannula and the radiofrequency probe is solved by ensuring contact between the probe and inner wall of the cannula. Contact may be achieved by providing a probe with a displacement from the centerline of the probe which is greater than the diameter of the cannula, such that the probe is assured of making contact with the inner wall of the cannula. An alternative solution to the problem of unreliable or poor contact may involve a biasing member positioned inside the lumen of the cannula such that a straight probe is biased outwards from the centerline of the probe, making contact with the inner wall of the cannula. Contact may also be achieved by modifying the straight probe body to have a section with an increase in diameter. The section with the increased diameter will contact the inner wall of the cannula, resulting in electrical communication between the two.

In some embodiments of the present disclosure, the present inventors have discovered and invented an electrosurgical apparatus for creating lesions in a tissue comprising a puncturing member and a probe. The puncturing member comprises a body with a proximal portion and distal portion. The distal portion of the body of the puncturing member has a conductive tip while the proximal portion has a hub. A lumen is defined by the body and the hub, extending along the length of the puncturing member. The probe comprises a handle at the proximal end that connects via connecting means to the puncturing member hub. The probe body, which is dimensioned to extend through the lumen of the puncturing member, comprises at least one displacement portion. The displacement portion of the probe body is biased to contact that inner wall of the puncturing member when the probe is disposed within the lumen of the puncturing member. This contact between the probe body and inner wall of the puncturing member enables energy to be delivered from the probe to the conductive tip of the puncturing member.

Some embodiments of the present disclosure provide an electrosurgical device insertable into a lumen of a puncturing member wherein the puncturing member comprises a hub and a conductive distal tip with the lumen extending from the hub to the distal tip. The electrosurgical device has a body comprised of a conductive material. The electrosurgical device's body comprises at least one displacement portion. The displacement portion of the body is biased to contact that inner wall of the puncturing member when the probe is disposed within the lumen of the puncturing member. This contact between the body and inner wall of the puncturing member enables energy to be delivered from the device to the conductive tip of the puncturing member.

In some embodiments of the present disclosure. The inventors have discovered and invented a method of creating a lesion using an electrosurgical apparatus comprising a puncturing member and a probe. The puncturing member comprises a hub at a proximal end, a conductive distal tip, and a lumen extending from the hub to the conductive distal tip. The probe includes a proximal end handle connected to a high energy generator and a probe body extending from the handle. The probe body comprises at least one displacement portion. The electrosurgical device's body comprises at least one displacement portion. The displacement portion of the body is biased to contact that inner wall of the puncturing member when the probe is disposed within the lumen of the puncturing member. This contact between the body and inner wall of the puncturing member enables energy to be delivered from the probe to the conductive tip of the puncturing member. The method of creating a lesion involves a first step of inserting the puncturing member into a patient. This first step is followed by positioning the puncturing member such that the conductive distal tip of the puncturing member is located at a target anatomical site. The next step involves inserting the probe at the proximal end of the puncturing member into the lumen of the puncturing member which is followed by delivering high frequency energy to the probe such that energy is delivered to the distal tip of the puncturing member. The delivery of energy creates a lesion in the target anatomical site through the delivery of high frequency energy at the distal tip of the puncturing member.

In some embodiments of the present disclosure, the inventors discovered and invented an electrosurgical apparatus for creating lesions in a tissue, comprising a puncturing member and a probe. The puncturing member comprises a body with a proximal portion and distal portion. The distal portion of the body of the puncturing member has a conductive tip while the proximal portion has a hub. A lumen is defined by the body and the hub, extending along the length of the puncturing member. A biasing member is positioned inside the lumen of the puncturing member. The probe comprises a handle at the proximal end that connects via connecting means to the puncturing member hub. The probe body, which is dimensioned to extend through the lumen of the puncturing member. The probe body interacts with the biasing member, such that the biasing member biases the probe body to contact the inner wall of the puncturing member. This contact between the probe body and inner wall of the puncturing member enables energy to be delivered from the probe to the conductive tip of the puncturing member.

Some embodiments of the present disclosure, the present inventors have discovered and invented an electrosurgical device insertable into a lumen of a puncturing member. The puncturing member comprises a hub and a conductive distal tip with the lumen extending from the hub to the distal tip. The electrosurgical device comprises a body with at least one section comprising a circumferential spacer. The circumferential spacer is comprised of a layer of conductive material that is dimensioned to fill the lumen of the puncturing member, making contact with an inner wall of the puncturing member. This contact between the body and inner wall of the puncturing member enables energy to be delivered from the device to the conductive tip of the puncturing member.

With reference now to the figures in detail, it is stressed that the particulars shown are by way of example, not drawn to scale, and for purposes of illustrative discussion of certain embodiments of the present disclosure only. Before explaining at least one embodiment of the disclosure in detail, it is to be understood that the disclosure is not limited in its application to the details of construction and the arrangement of the components set forth in the following description or illustrated in the figures. The disclosure is capable of other embodiments or of being practiced or carried out in various ways. Also, it is to be understood that the phraseology and terminology employed herein is for the purpose of description and should not be regarded as limiting.

Figure 1:
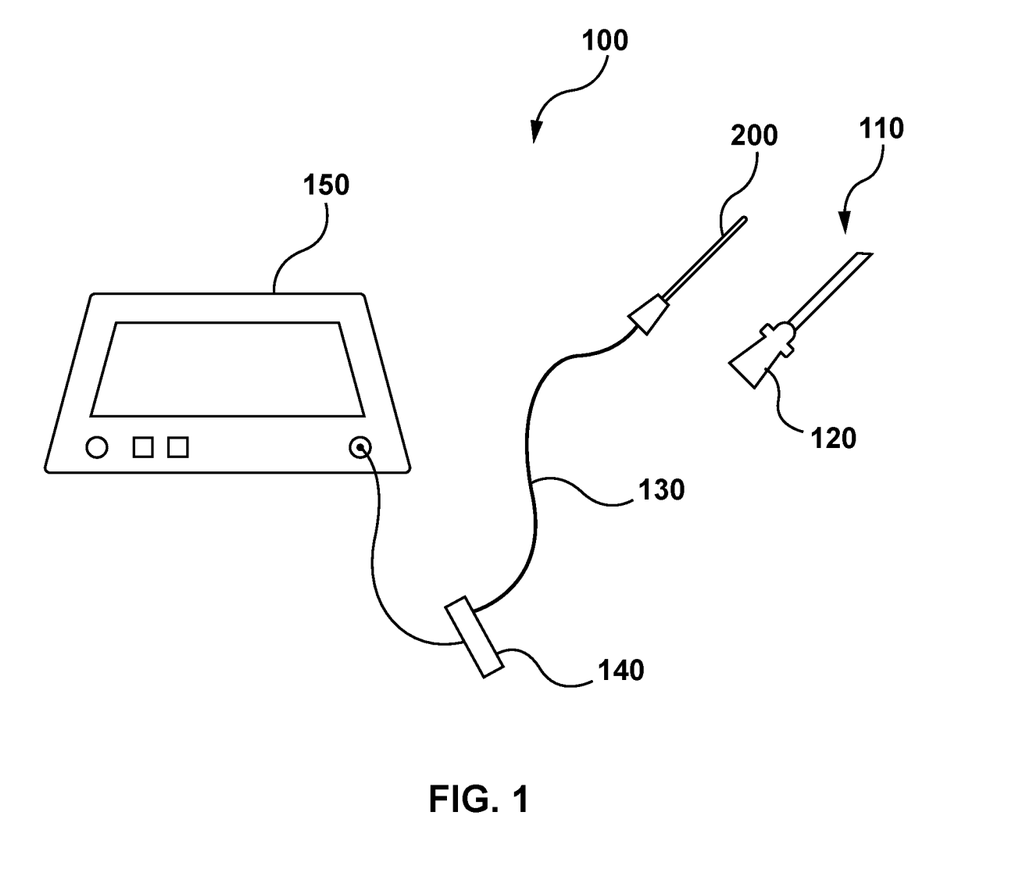
FIG. 1 is an illustration of an embodiment of the system including a radiofrequency energy generator, a puncturing member, and a probe.

FIG. 1 illustrates an embodiment of an exemplary system 100 and method that may be used during a radiofrequency ablation treatment procedure. A puncturing member, for example a cannula 110, is used to puncture the patient's skin and create a pathway to the target nerve. The cannula is made of a conductive material and may end in a sharp bevel or blunt end. In some embodiments, the cannula comprises an outer insulative layer, leaving only the electrically conductive distal tip of the cannula exposed. The cannula includes a hub 120 which has an aperture connecting to a lumen which extends the length of the cannula. A stylet (not shown) may be used in combination with the cannula, where the stylet is adapted to be inserted through the hub aperture and traverse the lumen of the cannula. A benefit to the insertion of a stylet is to prevent tissue from entering the lumen of the cannula 110 during the puncturing phase of the procedure, as the stylet diameter is dimensioned to substantially block the lumen when inserted therethrough. The distal tip of the stylet occludes the opening at the distal end of the cannula to prevent coring of the tissue during the puncture. Coring occurs when the puncturing device has a hollow lumen such that when the puncturing device is advanced through tissue, a core of tissue is dislodged. The stylet acts to block the opening at the distal end of the cannula to prevent the tissue from being dislodged during the puncture. The stylet comprises a stylet hub which mates with the cannula hub 120. The stylet is dimensioned such that a distal tip of the stylet is exposed from the cannula when the stylet hub is mated with the cannula hub. The distal tip of the stylet is configured to puncture skin and tissue. Once the cannula 110 and stylet have been inserted into the patient, various imaging techniques (e.g., fluoroscopy or ultrasound) may be used to confirm the location of the distal tip of the cannula 110.

Once the distal tip of the cannula 110 is in position (i.e., at a target nerve), the stylet may be removed from the cannula 110. In some embodiments, means for delivering fluid (such as a syringe) mates with the cannula hub 120 to optionally allow fluid (such as an anaesthetic) to be delivered to the target site. The fluid may be injected through the lumen of the cannula 110 and delivered to the target site if such is needed. The fluid delivery means is removed once the injection is completed and may be replaced by a probe 200. Alternatively, fluid retrieval means may mate with the cannula hub 120 to optionally allow fluid (such as blood) to be retrieved from the target site.

The probe 200 comprises a conductive probe body 210 and a handle 220. The probe handle 220 mates with the cannula hub 120 as the probe shaft is inserted through the hub 120 aperture into the cannula lumen. The probe handle 220 is connected via a connector cable 130 to a cable hub 140 which in turn is connected to a signal generator 150 capable of generating radiofrequency energy. Once inserted, the probe body 210 makes contact with the inner wall of the cannula 110, resulting in conductive communication between the probe body 210 and inner wall of the cannula 110. When the probe 200 is in place, the generator 150 may be turned on to send radiofrequency energy to the probe 200 which passes from the probe body 210 to the cannula tip and into the target tissue.

Various embodiments of a probe 200 are shown in FIGS. 2A-2D. In an exemplary embodiment, the probe comprises a probe body 210 and a handle 220. The probe body 210 may be formed of any conductive material such as stainless steel or nitinol. Nitinol's super-elasticity allows the probe to be durable, preventing kinking and permanent bending which may occur during insertion and removal of the probe 200 in to and out of the cannula.

In one embodiment, the probe body 210 may comprise a shaft defining a lumen (not shown), such as a hypotube. The lumen of the probe body 210 may contain internal wiring 240 that connects to a sensor 250 at the distal tip 260 of the probe body 210. The sensor 250 may be used to provide the user with additional information during the procedure. In one embodiment, the sensor may be a temperature detecting sensor, such as a thermocouple. The thermocouple may be either a K-type, with two dissimilar materials forming the internal wiring and ending in a junction, or a modified T-type, which would use one material in the internal wiring coupled with the probe body as the other dissimilar material. The temperature detecting sensor would allow measurement of temperature at or proximal to the distal tip 260 of the probe 200, providing information on how the ablation of tissue is progressing.

Figure 2A:
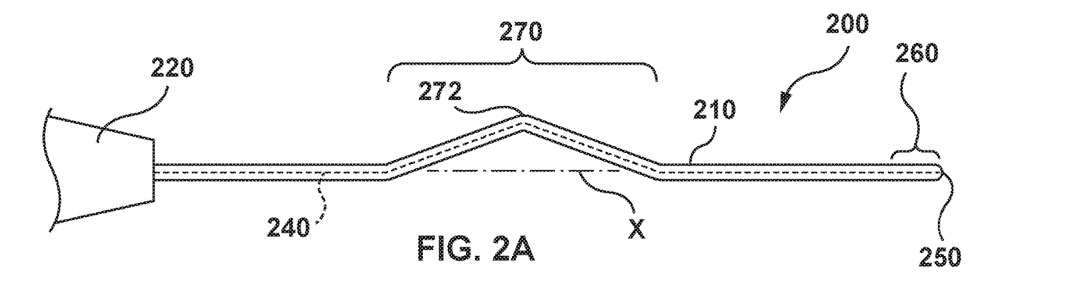
FIG. 2A is an illustration of an embodiment of a probe comprising a bent portion.
Figure 2B:
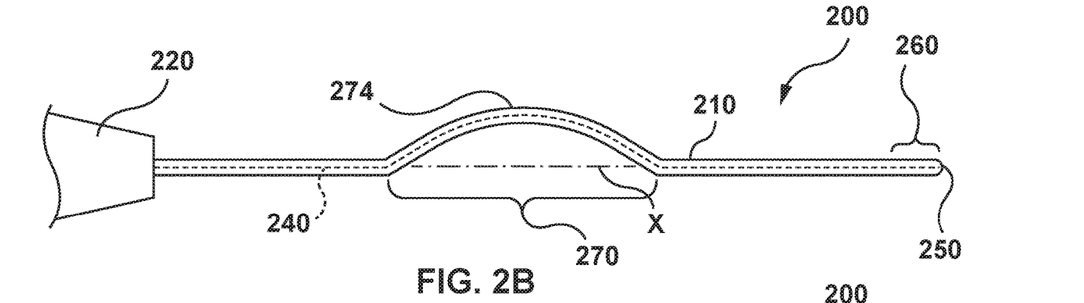
FIG. 2B is an illustration of an embodiment of a probe comprising a curved portion.
Figure 2C:
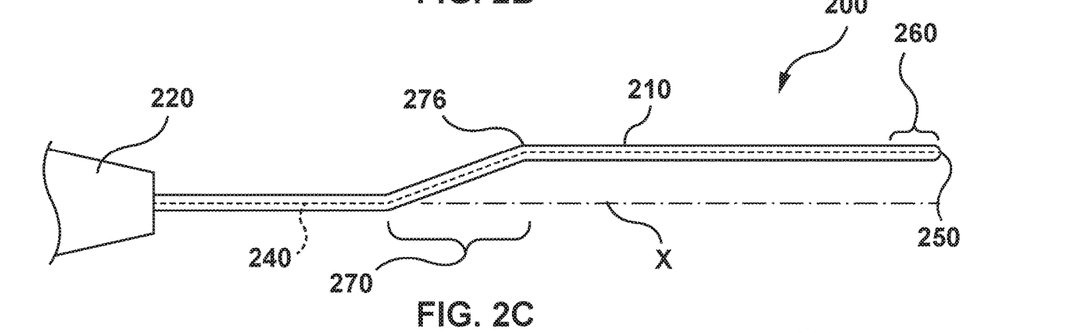
FIG. 2C is an illustration of an embodiment of a probe comprising an offset bend portion.
Figure 2D:
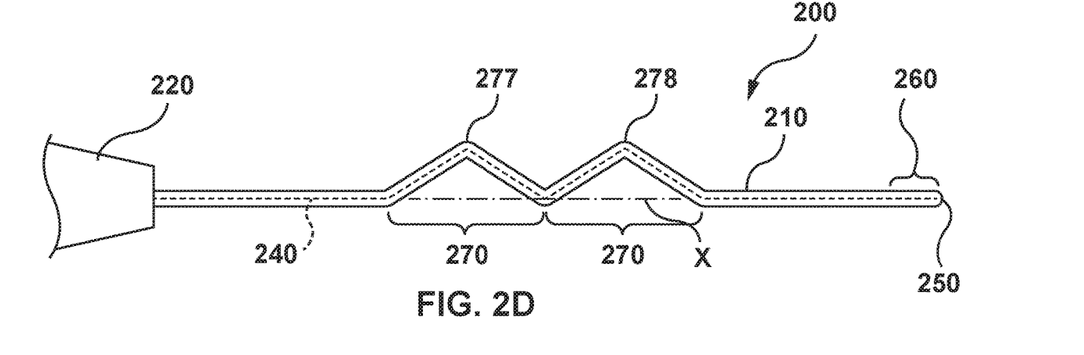
FIG. 2D is an illustration of an embodiment of a probe comprising multiple bent portions.

In one embodiment, the probe body 210 includes a displacement portion 270 being displaced outwardly from the centerline X of the probe. This displacement may be in the form of a bend 272 (FIG. 2A), curve 274 (FIG. 2B), or a bend offset 276 (FIG. 2C), for example. Other embodiments of the disclosure may include multiple displacement portions 270 along the probe body, one example may include multiple bends 277, 278 forming a saw-toothed section as illustrated in FIG. 2D.

Figure 3:
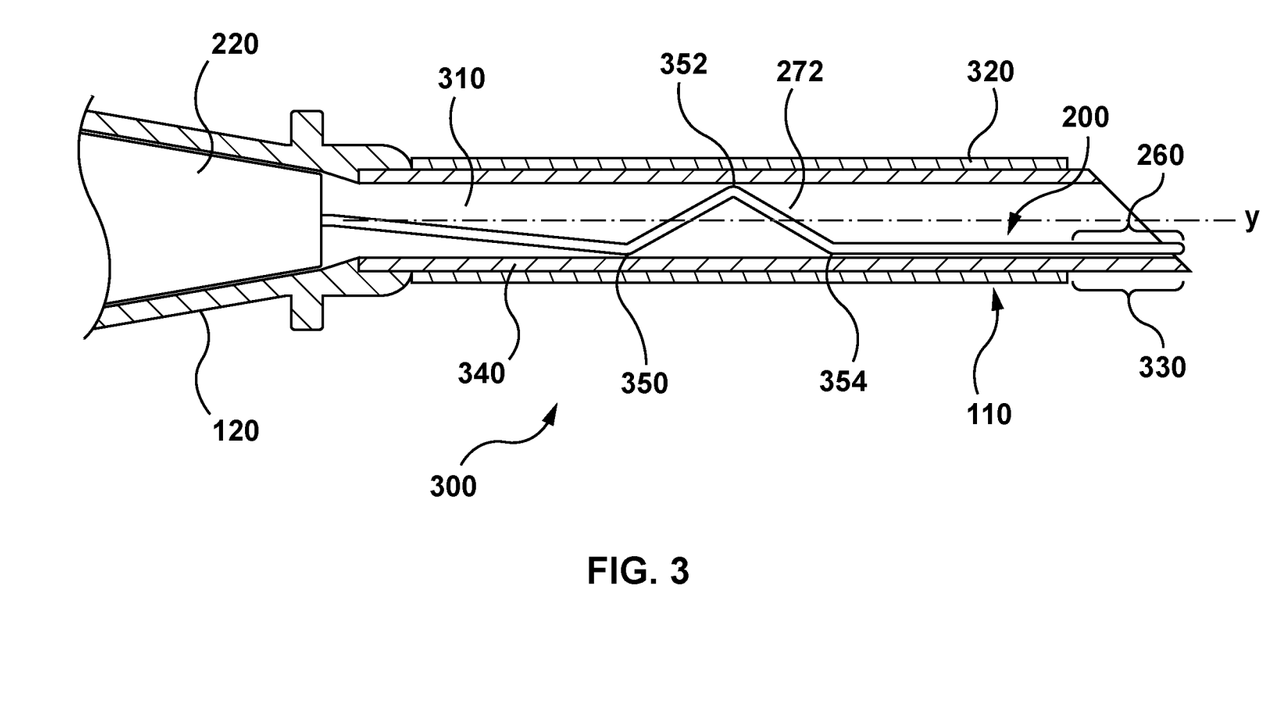
FIG. 3 is an illustration of the embodiment of the probe from FIG. 2a inserted through a puncturing member lumen.

An electrosurgical apparatus 300 for creating lesions in a tissue is shown in FIG. 3. The apparatus includes the probe 200 (the same embodiment illustrated in FIG. 2A) and a cannula 110. The cannula 110 is comprised of a conductive material, such as stainless steel. The cannula 110 comprises a hypotube defining a lumen 310 therethrough. The centerline of the lumen of the cannula defines a longitudinal axis Y. In some embodiments the cannula 110 comprises a proximal portion which may comprise an insulative material 320, such as polyethylene terephthalate (PET) or polymide, or any other insulative material, leaving the distal tip of the cannula exposed forming a conductive tip 330. The insulative layer 320 may be applied as a coating, heat shrink, or glued onto the cannula body 340. This embodiment enables the delivery of radiofrequency energy directly to the target tissue via the conductive tip 330 of the cannula 110.

In some embodiments the distal conductive tip 330 of the cannula 110 may form a sharp bevel, allowing users to pierce the skin of the patient to access the target nerve, or a blunt tip which may be used in cases with very sensitive anatomies. The cannula 110 further comprises a hub 120 which, in various embodiments, may be composed of acrylonitrile butadiene styrene (ABS), polysulfone (PSU), polyethylenimine (PEI), or polyphenylsulfone (PPSU), or any other similar material known in the art. The hub 120 includes a hub aperture which allows components (e.g., a stylet, syringe, or probe) or fluid (e.g., local anesthetics or blood) to pass through the lumen of the cannula 110. The hub 120 further comprises connector means that mate with other components of the system (e.g., a stylet, syringe, or probe) in the form of a Luer slip interaction between a male and female end, a Luer lock twist, a snap feature, or any other connector means that is air and water tight.

During operation, the probe 200 is inserted into the aperture of the cannula hub 120, extending the length of the lumen 310 of the cannula 110 such that the distal tip of the probe 260 is proximate the conductive tip 330 of the cannula 110. The probe handle 220 fits into the cannula hub 120 through a Luer slip interaction between a male and female end, a Luer lock twist, a snap feature, or any other connector means that is air and water tight. In some embodiments, as illustrated in FIG. 3, the probe body 210 may comprise a displacement portion in the form of bend 272 such that when the probe 200 is inserted into the cannula 110 it creates contact between the probe body 210 and the inner wall of the cannula 110. In this embodiment, three contact points (350, 352, 354) are created forming a connection between the probe 200 and cannula 110. The contact points (350, 352, 354) restrict transverse movement of the probe body 210. In other words, the contact points (350, 352, 354) between the probe body 210 and the cannula 110 restrict the probe body 210 from movement perpendicular to the longitudinal axis Y. These contact points allow for the transfer of radiofrequency energy from the generator, through the probe 200 to the distal tip 330 of the cannula 110 and into the target tissue, forming a lesion. Once the appropriate sized lesion has been formed, the probe 200 is removed from the cannula 110. In one embodiment, the probe 200 is made of nitinol making it more durable, kink and deformation resistant as compared with probes made of other materials.

Figure 4A:
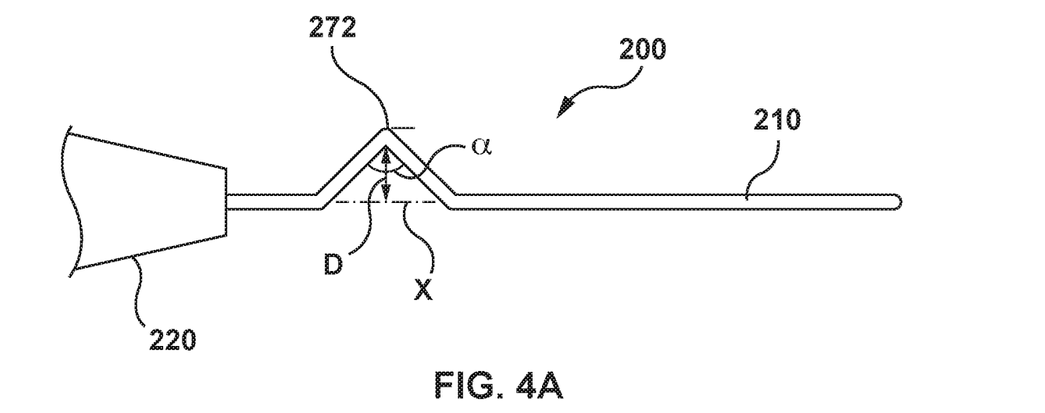
FIG. 4A is an illustration of a variation of the embodiment of a probe comprising a bent portion.
Figure 4B:
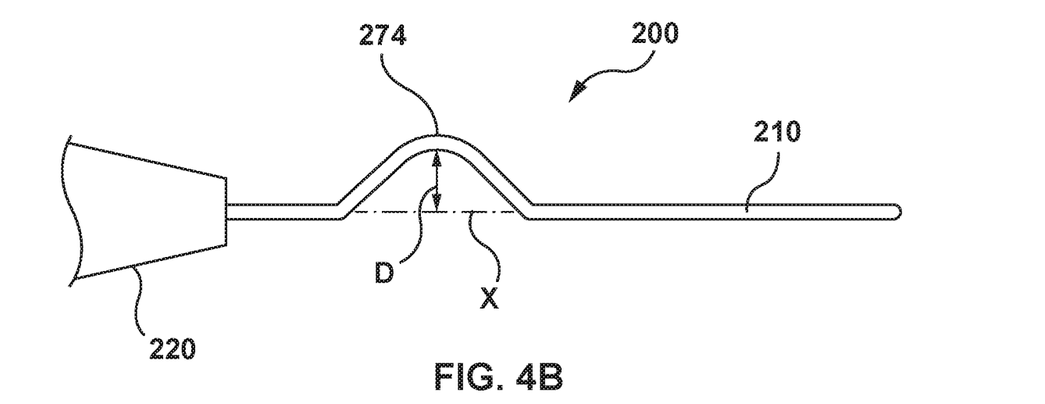
FIG. 4B is an illustration of a variation of the embodiment of a probe with a displacement portion comprising of a curve.
Figure 4C:
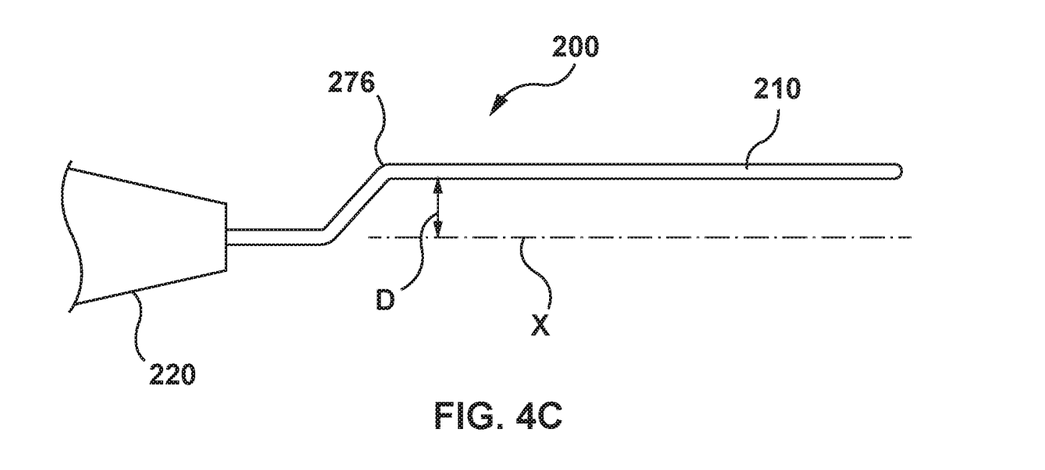
FIG. 4C is an illustration of a variation of the embodiment of a probe with a displacement portion comprising of an offset bend.
Figure 5A:
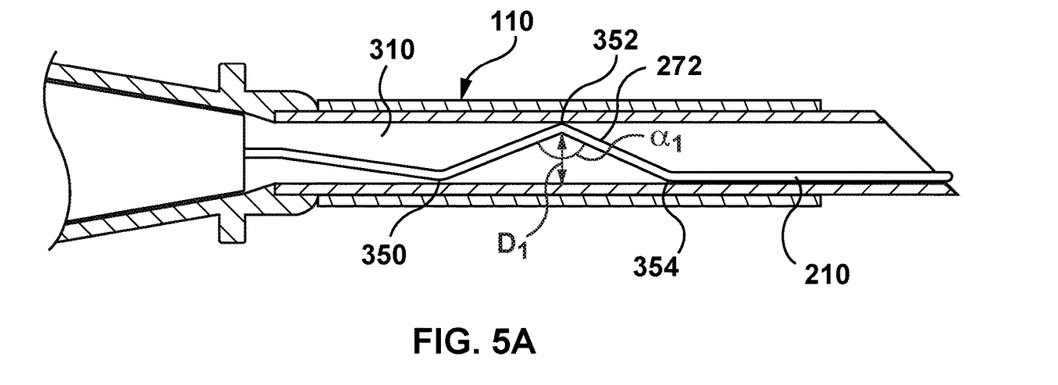
FIG. 5A is an illustration of the embodiment of the probe from FIG. 4a with a displacement portion comprising of a bend in a puncturing member.
Figure 5B:
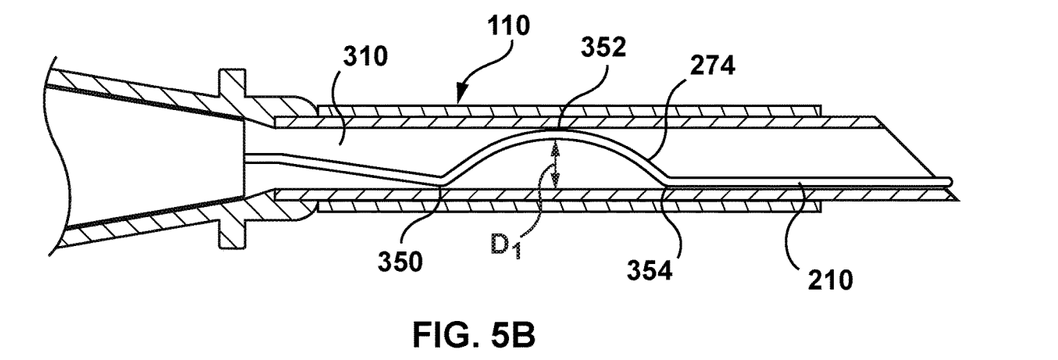
FIG. 5B is an illustration of the embodiment of the probe from FIG. 4b with a displacement portion comprising of a curve inserted into a puncturing member.
Figure 5C:
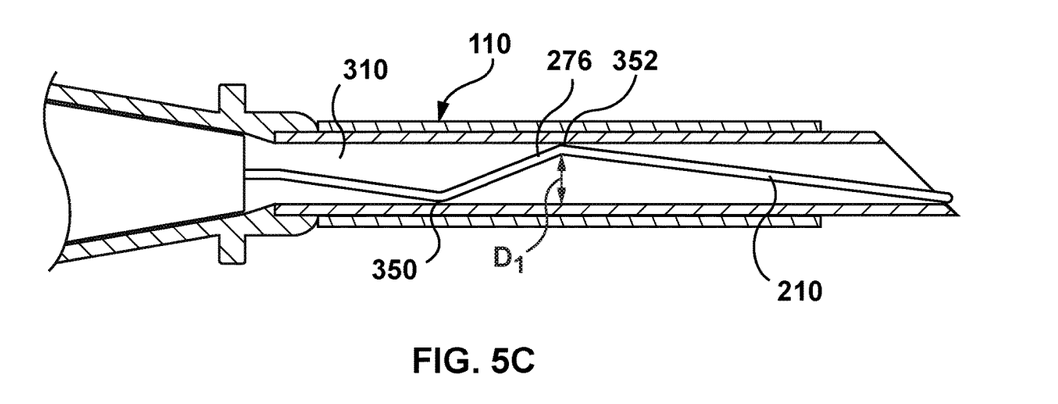
FIG. 5C is an illustration the embodiment of the probe from FIG. 4c with a displacement portion comprising of an offset bend inserted into a puncturing member.

During the manufacturing of the probe 200, the displacement portion of the probe body 210 may be modified to ensure contact between the inner wall of the cannula 110 and at least a portion of the probe body 210. FIG. 4 illustrates various examples of probes 200 and FIG. 5 illustrates the resulting interaction with the cannula 110 when inserted into the lumen 310.

In one embodiment of the probe 200, the displacement portion 270 may comprise a bend 272 (FIG. 4A). The distance D between the maximum point of the bend 272 and the centerline X of the probe is greater than the diameter of the lumen 310 of the cannula. In other words, the lumen 310 of the cannula is smaller in diameter than the outward displacement of the probe body's 210 bend 272. Accordingly, when the probe 200 is inserted into the cannula 110 (FIG. 5a), the inner wall of the cannula 110 restricts the outward displacement of the probe 200, reducing the distance D (i.e., D>$D_1$) and increasing the bend angle (i.e., α<$α_1$). The result is at least two points of contact (350, 352, 354) between the probe body 210 and the inner wall of the cannula 110.

In another embodiment, the displacement portion may comprise a curve 274. The distance D between the centerline X of the probe and the point of the curve 274 farthest from the centerline X of the probe can be larger than the diameter of the lumen of the cannula (FIG. 4b). When the probe 200 is inserted into the cannula 110, the inner wall of the cannula restricts the outward displacement of the probe 200, reducing the distance D (i.e., D>$D_1$) (FIG. 5b). This restriction leads to multiple points of contact (350, 352, 354) between the probe body 210 and the inner wall of the cannula 110.

In an alternative embodiment, the displacement portion 270 may comprise a bend offset 276 where the distance D between the maximum point of the offset 276 and the centerline X of the probe is larger than the diameter of the lumen 310 of the cannula (FIG. 4C). When the probe 200 is inserted into the cannula 110, the inner wall of the cannula 110 restricts the outward displacement of the probe body 210, reducing the distance D (i.e., D>$D_1$). This restriction leads to multiple points of contact (350, 352) between the probe body 210 and the inner wall of the cannula 110.

Figure 8:
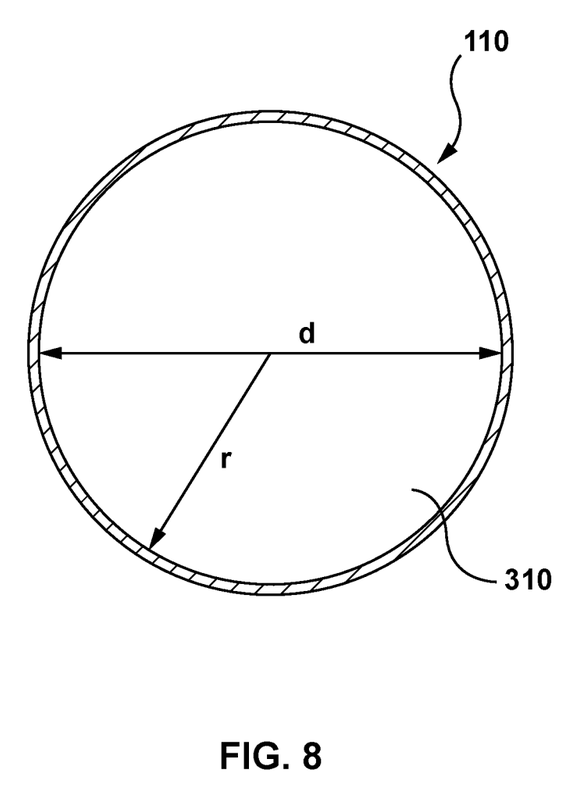
FIG. 8 is a cross sectional view of a puncturing member according to an embodiment.

In an alternative embodiment, the distance of displacement D from the centerline X of the probe (as seen in FIGS. 4A-4C) can range from the radius r of the puncturing member lumen and the diameter d of the puncturing member lumen, as seen in FIG. 8.

In the embodiments described above, the resulting contact between cannula 110 and probe 200, as seen in FIG. 3 and FIG. 5, is consistent and reliable, resulting in consistent and reliable delivery of high frequency energy from the probe 200 to the cannula 110.

During RFA, various cannula sizes may be used, depending on the desired size of lesion. Cannula (i.e., puncturing member) gauges range from as small as 22G up to 16G. In order to simplify the procedure, a single probe may be dimensioned to contact the inner wall of the cannula, regardless of the cannula gauge. This may be achieved by manufacturing the probe displacement portion to have a distance between the maximum point of displacement and the centerline of the probe equal to or greater than the lumen diameter of the largest gauge cannula. This would ensure contact between the probe and inner wall of the cannula, regardless of the gauge of cannula used. Additionally, the larger the displacement from the centerline of the probe, the greater the contact force between the probe and inner wall of the cannula. However, increasing the distance between the maximum point of the displacement and the centerline of the probe may lead to difficulty inserting and removing the probe. As a result, more force may be required to insert and remove the probe, leading to wear on both probe and cannula.

In some embodiments, the probe body may be comprised of a material with super-elastic properties, such as nitinol, which would allow the probe body to be more robust and durable, preventing kinking and permanent deformation. The location of the displacement portion may be located anywhere along the probe body, for example the displacement portion may be located proximate to the probe handle, in the proximal portion of the probe body, or at a distal portion of the probe body.

Figure 6:
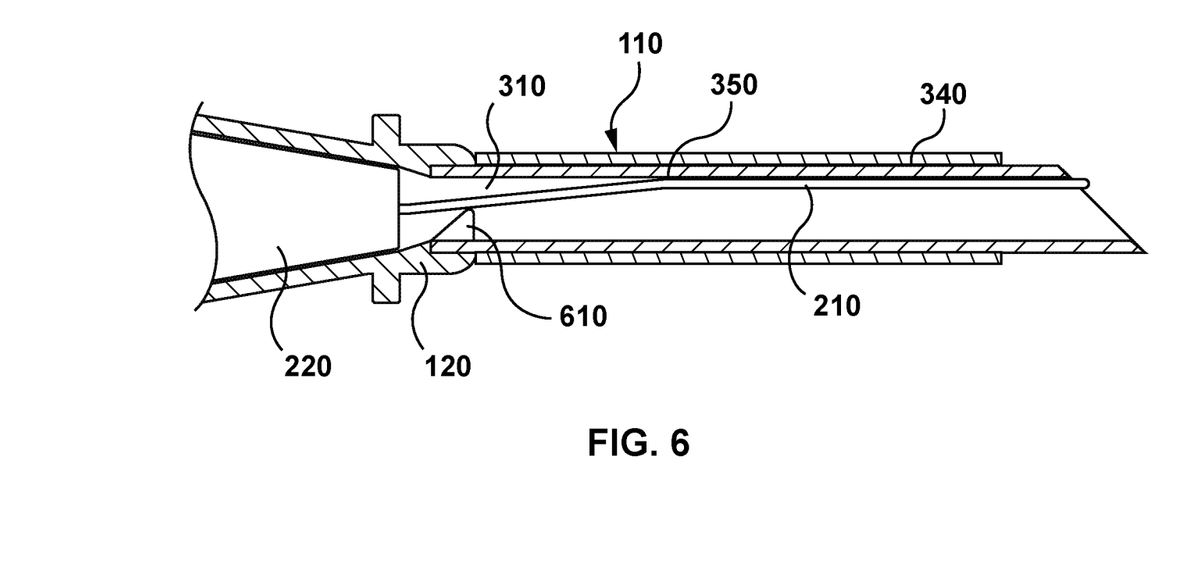
FIG. 6 is an illustration of an embodiment of an apparatus with a biasing member in the lumen of the puncturing member.

In an alternative embodiment of the electrosurgical apparatus, as illustrated in FIG. 6, the probe 200 may comprise a straight probe body 210. In this embodiment, the cannula 110 may comprise a biasing member 610 that interacts with the probe body 210 when the probe is inserted into the cannula 110. This biasing member 610 may be located at the intersection between the cannula hub 120 and the cannula lumen 310 or along the inner wall of the cannula 110. The biasing member 610 may take any form, such as a ramp or semi-circle, which pushes the probe body 210 off center. The probe body 210 may be flexible as a result of the small gauge size (i.e., 28G), and thus is displaced outward, making contact with the inner wall of the cannula 110 upon insertion. In some embodiments of this design, the probe body 210 may be made of a super-elastic, conductive material such as nitinol which would prevent the probe body from permanently deforming or kinking during the insertion and removal of the probe during the procedure.

Figure 7A:
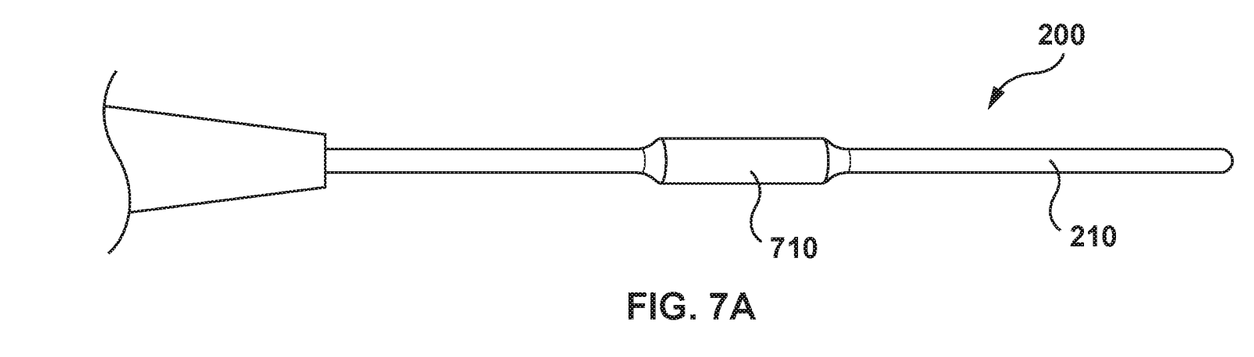
FIG. 7a is an illustration of an embodiment of a probe with a section of increased diameter.
Figure 7B:
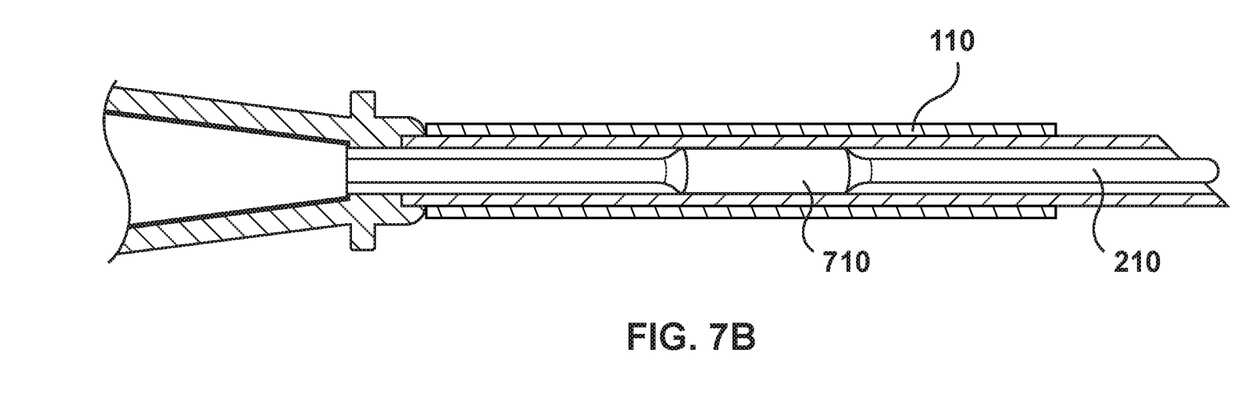
FIG. 7b is an illustration of an embodiment of a probe with a section of increased diameter inside the lumen of a puncturing member.

FIGS. 7A-7B illustrate another embodiment of the electrosurgical apparatus. In this embodiment the probe body 210 may comprise a displacement portion 270 being displaced outwardly from the centerline X of the probe in the form of a circumferential spacer 710. In an embodiment, the circumferential spacer 710 may comprise a layer of conductive material wrapped around the probe body 210 (FIG. 7A). The thickness of the circumferential spacer 710 will vary depending on the size of cannula used during the procedure. The location of the section with a circumferential spacer 710 may be located anywhere along the probe body 210 and may span any length along the probe body 210. Furthermore, in an alternate embodiment, the probe body 210 may comprise multiple sections with circumferential spacer 710 along the probe body 210. When the probe 200 is inserted into the cannula 110 (FIG. 7B), the circumferential spacer will make contact with the inner wall of the cannula, providing a contact point to deliver the radiofrequency energy from the probe body 210 to the cannula 110 and into the target tissue. In an embodiment, the diameter of the circumferential spacer 710 is substantially similar to the diameter of the inner wall of the cannula 110.

Further Examples: 1. An electro surgical apparatus for creating lesions in a tissue comprising:
 a puncturing member comprising:
  a body comprising a proximal portion and distal portion, wherein the distal portion comprises a conductive tip;
  a hub proximal of the body, comprising a connecting means; and
  a lumen defined by the body and the hub, wherein the lumen extends along the length of the puncturing member; and
 a probe comprising:
  a probe body, wherein the probe body is dimensioned to extend through the lumen of the puncturing member, and wherein the probe body comprises at least one displacement portion; and
  a handle at a proximal end of the probe;
 wherein, when the at least one displacement portion of the probe is disposed within the lumen of the puncturing member, the at least one displacement portion of the probe is biased to contact the inner wall of the puncturing member, whereby when the probe body contacts the inner wall, energy is delivered from the probe to the conductive tip of the puncturing member.

2. The apparatus of example 1, wherein when the probe is not disposed within the lumen of the puncturing member, the at least one displacement portion of the probe body is displaced from a longitudinal axis of the lumen.

3. The apparatus of example 2, wherein the longitudinal axis of the lumen is defined by the centerline of the lumen.

4. The apparatus of example 2, wherein the at least one displacement portion of the probe body is displaced from the longitudinal axis of the lumen by a distance greater than a diameter of the lumen of the puncturing member.

5. The apparatus of example 2, wherein the at least one displacement portion of the probe body is displaced from the longitudinal axis of the lumen by a distance ranging from a radius of the lumen of the puncturing member to a diameter of the lumen of the puncturing member.

6. The apparatus of any one of examples 1-5, wherein the at least one displacement portion of the probe body comprises a bend.

7. The apparatus of any one of examples 1-5, wherein the at least one displacement portion of the probe body comprises a curve.

8. The apparatus of any one of examples 1-5, wherein the at least one displacement portion of the probe body comprises an offset bend.

9. The apparatus of any one of examples 1-8, wherein the probe body comprises a lumen.

10. The apparatus of any one of examples 1-9, wherein the distal tip of the probe body comprises temperature sensing device.

11. The apparatus of examples 10, wherein the temperature sensing device is a thermocouple.

12. The apparatus of any one of examples 1-11, wherein the at least one displacement portion of the probe body is located in a proximal portion of the probe body.

13. The apparatus of any one of examples 1-12, wherein the lumen comprises a biasing member, and wherein the probe body interacts with the biasing member such that the biasing member biases the probe body to contact the inner wall of the puncturing member, whereby when the probe body contacts the inner wall, energy is delivered from the probe to the conductive tip of the puncturing member.

14. The apparatus of example 13 wherein the biasing member is positioned in the lumen of the puncturing member.

15. The apparatus of any one of examples 13 and 14, wherein the biasing member comprises a ramp.

16. The apparatus of any one of examples 13 and 14, wherein the biasing member comprises a semi-circle.

17. The apparatus of any one of examples 1-16, wherein the distal tip of the puncturing member ends in a bevel.

18. The apparatus of any one of examples 1-17, wherein the proximal portion of the puncturing member body comprises an insulative layer.

19. The apparatus of any one of examples 1-18, wherein the connecting means comprises a Luer slip interaction.

20. The apparatus of any one of examples 1-19, wherein the probe body and the lumen of the puncturing member are dimensioned such that when the probe body is disposed within the lumen, the probe body is restricted from transverse movement.

21. An electrosurgical device insertable into a lumen of a puncturing member wherein the puncturing member comprises a hub and a conductive distal tip with the lumen extending from the hub to the distal tip, the electrosurgical device comprising:
a body comprised of a conductive material, wherein the body comprises at least one displacement portion wherein when the at least one displacement portion of the probe is disposed within the lumen of the puncturing member, the at least one displacement portion of the probe is biased to contact the inner wall of the puncturing member, whereby when the body contacts an inner wall of the puncturing member, energy is delivered from the body to the conductive tip of the puncturing member.

22. The device of example 21, wherein when the device is not inserted into the lumen of the puncturing member, the at least one displacement portion of the body is displaced from a longitudinal axis of the lumen.

23. The device of example 22, wherein the longitudinal axis of the lumen is defined by the centerline of the lumen.

24. The device of example 22, wherein the at least one displacement portion of the probe body is displaced from the longitudinal axis of the lumen by a distance greater than a diameter of the lumen of the puncturing member.

25. The device of example 22, wherein the at least one displacement portion of the probe body is displaced from the longitudinal axis of the lumen by a distance ranging from a radius of the lumen of the puncturing member to a diameter of the lumen of the puncturing member.

26. The device of any one of examples 21-25, wherein the at least one displacement portion of the body comprises a bend.

27. The device of any one of examples 21-25, wherein the at least one displacement portion of the body comprises a curve.

28. The device of any one of examples 21-25, wherein the at least one displacement portion of the body comprises an offset bend.

29. The device of any one of examples 20-28, wherein the at least one displacement portion of the body is located in a proximal portion of the probe body.

30. The device of any one of examples 20-29, wherein a distal tip of the body comprises a temperature sensing device.

31. The device of example 30, wherein the temperature sensing device is a thermocouple.

32. The device of any one of examples 21-30, wherein the device is comprised of nitinol.

33. The device of any one of examples 21-30, wherein the body and the lumen of the puncturing member are dimensioned such that when the body is disposed within the lumen, the probe body is restricted from transverse movement.

34. The method of creating a lesion using an electro surgical apparatus comprising a puncturing member and a probe, wherein the puncturing member comprises a hub at a proximal end, a conductive distal tip, and a lumen extending from the hub to the conductive distal tip and wherein the probe comprises a proximal end handle connected to a high energy generator and a probe body extending from the handle, the method comprising:
inserting the puncturing member into a patient;
positioning the conductive distal tip of the puncturing member at a target anatomical site;
inserting the probe at the proximal end of the puncturing member into the lumen of the puncturing member, wherein the probe body comprises at least one displacement portion;
wherein, when the at least one displacement portion of the probe body is disposed within the lumen of the puncturing member, the at least one displacement portion of the probe body is biased to contact an inner wall of the puncturing member, whereby when the probe body contacts the inner wall, energy is delivered from the probe to the conductive tip of the puncturing member; and,
delivering high frequency energy to the probe such that energy is delivered to the distal tip of the puncturing member; and,
creating the lesion in the target anatomical site through the delivery of high frequency energy at the distal tip of the puncturing member.

35. The method of example 34 wherein the at least one displacement portion of the probe comprises a bend.

36. The method of example 34, wherein the at least one displacement portion of the probe comprises a curve.

37. The method of example 34, wherein the at least one displacement portion of the probe comprises an offset bend.

38. The method of any one of examples 34-37, wherein the high frequency energy delivered comprises radiofrequency energy.

39. The method of any one of examples 34-38, wherein the probe body and the lumen of the puncturing member are dimensioned such that when the probe body is disposed within the lumen, the probe body is restricted from transverse movement.

40. An electrosurgical apparatus for creating lesions in a tissue, the electrosurgical apparatus comprising:
a puncturing member comprising:
a body comprising a proximal portion and distal portion, wherein the distal portion comprises a conductive tip;
a hub proximal of the body, comprising a connecting means; and
a lumen defined by the body and the hub, wherein the lumen extends along the length of the puncturing member;
a biasing member positioned inside the lumen; and
a probe comprising:
a probe body comprised of a conductive material, wherein the probe body is dimensioned to extend through the lumen of the puncturing member; and
wherein, the probe body interacts with the biasing member, such that the biasing member biases the probe body to contact an inner wall of the puncturing member, whereby when the probe body contacts the inner wall, energy is delivered from the probe to the conductive tip of the puncturing member; and, a handle at a proximal end of the probe;

41. The apparatus of example 40, wherein the biasing member is positioned in the lumen of the puncturing member.

42. The apparatus of any one of examples 40 and 41, wherein the biasing member comprises a ramp.

43. The apparatus of any one of examples 40 and 41, wherein the biasing member comprises a semi-circle.

44. An electrosurgical device insertable into a lumen of a puncturing member wherein the puncturing member comprises a hub and a conductive distal tip with the lumen extending from the hub to the distal tip, the electrosurgical device comprising:

a body comprised of at least one section with a circumferential spacer wherein the at least one circumferential spacer comprises a layer of conductive material and wherein the at least one circumferential spacer fills the lumen of the puncturing member, making contact with an inner wall of the puncturing member, whereby when the body contacts the inner wall, energy is delivered from the probe to the conductive tip of the puncturing member.

The embodiments of the disclosure described above are intended to be exemplary only. The scope of the disclosure is therefore intended to be limited solely by the scope of the appended claims.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

Although the disclosure has been described in conjunction with embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An electrosurgical apparatus for creating lesions in a tissue comprising:
    a puncturing member comprising:
        a body comprising a proximal portion and distal portion, wherein the distal portion comprises a conductive tip;
        a hub proximal of the body, comprising a connecting means; and
        a lumen defined by the body and the hub, wherein the lumen extends along the length of the puncturing member; and
    a probe comprising:
        a handle at a proximal end of the probe; and
        a probe body, wherein the probe body is dimensioned to extend through the lumen of the puncturing member, and wherein the probe body comprises at least one displacement portion positioned between the proximal end and a distal end of the probe,
        wherein, when the at least one displacement portion of the probe is disposed within the lumen of the puncturing member, the at least one displacement portion of the probe is biased to contact an inner wall of the puncturing member, whereby when the probe body contacts the inner wall, energy is delivered from the probe to the conductive tip of the puncturing member.

2. The apparatus of claim 1, wherein when the probe is not disposed within the lumen of the puncturing member, the at least one displacement portion of the probe body is displaced from a longitudinal axis of the lumen.

3. The apparatus of claim 2, wherein the at least one displacement portion of the probe body is displaced from the longitudinal axis of the lumen by a distance greater than a diameter of the lumen of the puncturing member.

4. The apparatus of claim 2, wherein the at least one displacement portion of the probe body is displaced from the longitudinal axis of the lumen by a distance ranging from a radius of the lumen of the puncturing member to a diameter of the lumen of the puncturing member.

5. The apparatus of claim 2, wherein the at least one displacement portion of the probe body is selected from the group consisting of a bend, a curve, or an offset bend.

6. An electrosurgical device insertable into a lumen of a puncturing member wherein the puncturing member comprises a hub and a conductive distal tip with the lumen extending from the hub to the distal tip, the electrosurgical device comprising:

a body comprised of a conductive material, wherein the body comprises at least one displacement portion positioned between a proximal end and a distal end of the body, wherein when the at least one displacement portion of the body is disposed within the lumen of the puncturing member, the at least one displacement portion of the body is biased to contact an inner wall of the puncturing member, whereby when the body contacts the inner wall of the puncturing member, energy is delivered from the body to the conductive tip of the puncturing member.

7. The device of claim 6, wherein when the device is not inserted into the lumen of the puncturing member, the at least one displacement portion of the body is displaced from a longitudinal axis of the lumen.

8. The device of claim 7, wherein the at least one displacement portion of the probe body is displaced from the longitudinal axis of the lumen by a distance greater than a diameter of the lumen of the puncturing member.

9. The device of claim 7, wherein the at least one displacement portion of the probe body is displaced from the longitudinal axis of the lumen by a distance ranging from a radius of the lumen of the puncturing member to a diameter of the lumen of the puncturing member.

10. The device of claim 6, wherein the at least one displacement portion of the body is selected from the group consisting of a bend, a curve, or an offset bend.

11. The device of claim 6, wherein the body and the lumen of the puncturing member are dimensioned such that when the body is disposed within the lumen, the probe body is restricted from transverse movement.

12. An electrosurgical apparatus for creating lesions in a tissue, the electrosurgical apparatus comprising:

a puncturing member comprising:
  a body comprising a proximal portion and distal portion, wherein the distal portion comprises a conductive tip;
  a hub proximal of the body, comprising a connecting means; and
  a lumen defined by the body and the hub, wherein the lumen extends along the length of the puncturing member;
a biasing member positioned inside the lumen and proximal the conductive tip, the biasing member extending from an inner surface of the body of the puncturing member; and
a probe comprising:
  a probe body comprised of a conductive material, wherein the probe body is dimensioned to extend through the lumen of the puncturing member; and
  wherein, the probe body interacts with the biasing member, such that the biasing member biases the probe body to contact an inner wall of the puncturing member, whereby when the probe body contacts the inner wall, energy is delivered from the probe to the conductive tip of the puncturing member; and,
  a handle at a proximal end of the probe.

13. The apparatus of claim 12, wherein the biasing member comprises a ramp.

14. The apparatus of claim 12, wherein the biasing member comprises a semi-circle.

15. The apparatus of claim 12, wherein the biasing member is positioned proximal the hub of the puncturing member.

* * * * *